United States Patent [19]
Greenwald et al.

[11] Patent Number: 5,738,846
[45] Date of Patent: Apr. 14, 1998

[54] INTERFERON POLYMER CONJUGATES AND PROCESS FOR PREPARING THE SAME

[75] Inventors: Richard B. Greenwald, Somerset; Carl W. Gilbert, Basking Ridge, both of N.J.

[73] Assignee: Enzon, Inc., Piscataway, N.J.

[21] Appl. No.: 561,616

[22] Filed: Nov. 21, 1995

Related U.S. Application Data

[63] Continuation-in-part of Ser. No. 337,567, Nov. 10, 1994.
[51] Int. Cl.$^6$ .................................................. A61K 38/21
[52] U.S. Cl. ................................ 424/85.7; 530/402
[58] Field of Search ......................... 424/85.7; 530/402

[56] References Cited

U.S. PATENT DOCUMENTS

| | | | |
|---|---|---|---|
| 4,179,337 | 12/1979 | Davis et al. | 435/181 |
| 4,275,000 | 6/1981 | Ross | 260/112 R |
| 4,609,546 | 9/1986 | Hiratani | 424/83 |
| 4,680,338 | 7/1987 | Sundoro | 525/54.1 |
| 4,766,106 | 8/1988 | Katre et al. | 514/12 |
| 4,894,226 | 1/1990 | Aldwin et al. | 424/85.2 |
| 4,904,582 | 2/1990 | Tullis | 435/6 |
| 4,917,888 | 4/1990 | Katre et al. | 424/85.91 |
| 4,935,465 | 6/1990 | Garman | 525/54.1 |
| 5,004,605 | 4/1991 | Hershenson et al. | 424/85.6 |
| 5,109,120 | 4/1992 | Ueno et al. | 530/351 |
| 5,122,614 | 6/1992 | Zalipsky | 548/520 |
| 5,281,698 | 1/1994 | Nitecki | 530/351 |
| 5,283,317 | 2/1994 | Saifer et al. | 528/405 |
| 5,382,657 | 1/1995 | Karasiewicz et al. | 530/351 |

FOREIGN PATENT DOCUMENTS

| | | |
|---|---|---|
| 0154316 | 9/1985 | European Pat. Off. |
| 0236987 | 9/1987 | European Pat. Off. |
| 05510356 | 10/1992 | European Pat. Off. |
| 0584876 | 3/1994 | European Pat. Off. |
| WO9101758 | 2/1991 | WIPO |
| WO9216555 | 10/1992 | WIPO |

OTHER PUBLICATIONS

Zalipsky, et al., Attachment of Drugs to Polyethlene Glycols, Eur. Polym. J., vol. 19, No. 12, pp. 1177–1183 (1983).

Pestka, Sidney "Interferon–α" Human Cytokines, 1992, B.B. Aggarwal et al. Editors, Blackwell Scientific Publications (18 pages).

Larocca, A. et al. "Human Interferon–β" Human Cytokines, 1992, B.B. Aggarwal et al. Editors, Blackwell Scientific Publications (15 pages).

J. Neugebauer "A Guide to the Properties and Uses of Detergents in Biology and Biochemistry", 1988 (34 pages).

*Primary Examiner*—Chhaya D. Sayala
*Attorney, Agent, or Firm*—Roberts & Mercanti, L.L.P.

[57] ABSTRACT

Interferon-polymer conjugate containing compositions having high levels of retained interferon activity and relatively long circulating lives in vivo are disclosed. The compositions contain a mixture of mono-interferon-polymer conjugates and bis-interferon-polymer conjugates, with both species containing substantially a single polymer strand. The conjugate compositions are prepared by reacting about 1 mole of an interferon with from about 0.125 to about 1 mole of a bis-activated substantially non-antigenic polymer under conditions sufficient to effect covalent conjugation of the interferon and polymer. Methods of treating interferon-susceptible conditions with the compositions of the present invention are also disclosed.

46 Claims, No Drawings

5,738,846

INTERFERON POLYMER CONJUGATES AND PROCESS FOR PREPARING THE SAME

CROSS-REFERENCE TO RELATED APPLICATIONS

This application is a continuation-in-part of U.S. patent application Ser. No. 08/337,567 filed Nov. 10, 1994, the disclosure of which is hereby incorporated by reference.

BACKGROUND OF THE INVENTION

The present invention is directed to long-acting interferon-containing preparations. In particular the invention is directed to compositions containing interferon conjugates containing a single polymeric strand.

Conjugating biologically-active proteins to polymers has been suggested to improve one or more of the properties of circulating life, water solubility or antigenicity in vivo. For example, some of the initial concepts of coupling peptides or polypeptides to polyethylene glycol (PEG) and similar water-soluble polymers are disclosed in U.S. Pat. No. 4,179,337, the disclosure of which is incorporated herein by reference. Conjugates are formed by reacting a biologically active material with a several fold molar excess of a polymer which has been modified to contain a terminal linking group.

Insulin and hemoglobin were among the first therapeutic agents conjugated. These relatively large polypeptides contain several free $\epsilon$-amine attachment sites. Several polymers could be attached without significant loss of biologic activity.

The conjugation process, however, is not without complications. Excessive polymer conjugation or reactions using molar excesses of polymers beyond certain ratios can result in inactive conjugates. Problems often result when a therapeutic moiety's active site (i.e. where groups associated with bioactivity are found) becomes blocked by polymer attachment. This problem can be difficult to avoid since the polymer and protein are typically joined in solution-based reactions. Pre-blocking the active sites with reversible materials such as pyridoxal phosphate has been suggested, but the results have been inconsistent. The problems are particularly acute with relatively lower molecular weight proteins and peptides. These bioactive materials often have few attachment sites not associated with bioactivity.

Interferons are a particular example of proteins which could benefit from improved polymer conjugation techniques. Several polymer-interferon conjugates have previously been suggested. See, for example, U.S. Pat. Nos. 4,766,106 and 4,917,888 which describe inter alia beta interferon conjugated with methoxypolyethylene glycol N-succinimidyl glutarate or methoxypolyethylene glycol N-succinimidyl succinate. The conjugation reactions were carried out using relatively high molar excesses (10, 20 and 50-fold) of the polymer. U.S. Pat. No. 5,382,657 also discloses interferon conjugates. In this reference, however, the conjugates are formed using mono-activated, alpha alkyl substituted PEG's and the polymer was reacted in molar excess with the interferon.

European Patent Application bearing publication No. 0 236 987 describes reacting alpha and gamma interferons with high molar excesses of alkyl imido ester-activated polyethylene glycols. European Patent Application bearing publication No. 0 510 356 describes conjugating alpha interferon with pyridinyl carbonyl and thiocarbonyl activated PEG. In both cases, however, the resultant conjugates included various species containing a wide variety pegylated species, including a substantial amount containing more than one polymer strand.

In spite of the above-described disclosures, the interferon-polymer conjugates have been unacceptable. One of the chief drawbacks has been that the level of retained interferon activity has been too low. In addition, isolating the particularly desired conjugated species from reaction mixtures containing conjugated species having varying degrees of polyethylene glycol substitution is time consuming and inefficient.

The present invention addresses these shortcomings.

SUMMARY OF THE INVENTION

One embodiment of the invention provides a process for preparing long-acting interferon-containing compositions. The process includes:

reacting about one mole of an interferon with about 0.125 to about one mole of a bis-activated, substantially non-antigenic polymer under conditions sufficient to effect covalent conjugation of the interferon and polymer without substantial loss of interferon activity and form a reaction mixture containing interferon-polymer conjugates which are predominately mono-interferon-polymer conjugates and bis-interferon-polymer conjugates. In preferred aspects of this embodiment, the bis activated polymer is present in amounts of from about 0.25 to about 0.75 moles per mole of interferon. Still further preferred embodiments of the inventive process include reacting about 0.25 to about 0.5 moles of bis-activated polymer per mole of interferon.

The substantially non-antigenic polymer is preferably a polyalkylene oxide such as a polyethylene glycol having a molecular weight of from about 600 to about 60,000. Other substantially non-antigenic polymers can also be used. Particularly preferred aspects of the invention include homobifunctional activated polymers such as bis-succinimidyl carbonate PEG. Other suitable linkage forming moieties include leaving groups such as succinimidyl activated esters, amines and so forth.

Additional aspects of this embodiment include the further optional steps of isolating the mono-interferon polymer species and bis-interferon polymer species in the reaction mixture from the unreacted interferon or polymer. The process can also include the additional step of separating the mono-interferon species from the bis-interferon species.

Another aspect of the invention includes conducting the conjugation reaction of the interferon and polymer in the presence of a surfactant.

In accordance with another embodiment of the present invention, there are provided interferon-polymer conjugate containing compositions. The compositions can be included as part of a pharmaceutically-acceptable solution which contains a mixture of mono-interferon-polymer conjugates and bis-interferon-polymer conjugates. The interferons included in the composition are covalently linked, such as via a carbamate or amide linkage, to the non-antigenic polymer. In one particularly preferred embodiment, the compositions contain primarily mono-interferon-polymer conjugates and bis-interferon-polymer conjugates.

The compositions of the present invention include interferons of all types such as alpha, beta and gamma interferons as well as all subtypes of the foregoing. Alpha interferons, however, are preferred.

The interferon-polymer conjugates included in the compositions of the present invention differ from interferon conjugates of the prior art in that substantially all of the mono- and bis-interferon species contain a single polymer strand covalently attached to the interferon. This is to be contrasted with other interferon-polymer conjugates which are prepared with molar excesses of mono-activated polymer and which therefore contain multiple species including a significant portion having more than one strand of polymer per interferon. Such multiple polymer conjugated interferon species have been demonstrated to have low levels of retained interferon activity.

The invention also includes methods of treating interferon susceptible conditions in mammals. In this aspect, the treatment methods include administering an effective amount of the compositions described herein containing the interferon conjugates to mammals requiring such therapy.

As a result of the present invention, highly active, long lasting interferon-containing conjugates are provided. In preferred embodiments, the conjugates provide predictable, uniform interferon activity due to the substantially uniform presence of a single strand of polymer per conjugate.

Another feature of the compounds of the present invention is that the increased circulating life is achieved with only minor losses in retained interferon activity. This is achieved by forming interferon conjugates using carefully controlled ratios of bis-activated polymer in relation to the interferon so that most polymers attach to interferon lysines in a less random manner and thus maximize uniform interferon bioactivity. The process of the present invention provides additional advantages over the processes of the prior art. In spite of using bis-activated polymers to effect attachment of the polymer to the interferon, the cross-linking into high molecular weight species comprising chains of alternating polymer and interferon expected to result is unexpectedly and substantially avoided due to the precise ratios of the respective reactants.

For purposes of the present invention, the term "bis" shall be understood to be related to polymers having both alpha and omega terminal moiety substitutions. "Bis-activated polymers" shall be understood to include polymers having alpha and omega terminal moieties which serve as suitable leaving groups during conjugation (linking) reactions with interferons.

"Bis-interferon-polymer conjugates" shall be understood to describe a single strand of substantially non-antigenic polymer with two molecules of interferon covalently attached, one to the alpha terminus and one to the omega terminus of the polymer. "Mono-interferon-polymer conjugates" shall be understood to describe a conjugate containing a single interferon molecule covalently attached to a terminus of a single strand of substantially non-antigenic polymer.

The term "interferon susceptible condition" shall be understood to include all disease states, such as viral infections, cancers, or related conditions, which benefit therapeutically from exogenous interferon administration. Details concerning such conditions are provided below in Section 6.

For a better understanding of the present invention, reference is made to the following description and its scope will be pointed out in the appended claims.

DETAILED DESCRIPTION OF THE INVENTION

1. INTERFERONS

The present invention includes interferons (IFN's) of all types. For example, the compositions and methods described herein can include alpha, beta and gamma interferons as well as all subtypes of the foregoing. The interferons can be isolated or extracted from a mammalian source such human, bovine or porcine specimens such as tissues. The interferons can also be prepared using recombinant techniques such as those using synthetic genes expressed in $E.\ coli$ and other techniques known to those of ordinary skill in the art. See, for example, Pestka, "Interferon $\alpha$" in *Human Cytokines*, Blackwell Scientific Publications 1–16 (1992), the disclosure of which is incorporated herein by reference. Alpha interferons ($\alpha$IFN) are preferred for the conjugates of the present invention. One particularly preferred $\alpha$IFN is IFN$\alpha$-2b, a recombinantly-made product of the Schering Plough Corp., Madison, N.J. Alternate embodiments of the invention include IFN's which are not completely autologous to those of the mammal in need of treatment, but nonetheless may be used since the polymeric modification sufficiently reduces antigenic responses, if any. A key, however, is that the non-autologous IFN has sufficient bioactivity or IFN effect such as antiviral activity in the target mammal. Other substances including IFN fractions or predecessor polypeptides can also be included in the conjugates of the present invention. As used herein, "IFN effect in mammals" relates to in vivo interferon activity corresponding to that observed with unmodified IFN's. These substances are prepared by using techniques known to those of ordinary skill in the art such as tissue culture, extraction from animal sources or by recombinant DNA methodologies. Transgenic sources of IFN and related moieties are also contemplated. Such materials are obtained from transgenic animals, i.e. mice, pigs, goats, cows, etc. where the IFN protein is expressed in milk, blood, or tissues. It is also understood that the recombinant techniques could also include a glycosylation site for addition of a carbohydrate moiety on the recombinantly-derived polypeptide. The method by which the IFN is prepared for the conjugates of the present invention is not limited to those described herein.

$\alpha$IFN has certain advantages over other interferon species such as $\beta$ and $\gamma$ IFN's. For purposes of the present invention, the $\alpha$IFN's are particularly preferred because of their biochemical and serological properties such as documented antiviral properties and effective bloodstream diffusion. It is to be understood, however, that the invention embraces all types of interferons.

2. NON-ANTIGENIC POLYMERS

In order to form the mon- and bis-interferon conjugates of the present invention, polymers such as poly(alkylene oxides) (PAO's) are converted into activated forms, as such term is known to those of ordinary skill in the art. Thus, one and preferably both of the terminal polymer hydroxyl end-groups, (i.e. the alpha and omega terminal hydroxyl groups) are converted into reactive functional groups which allows covalent conjugation. This process is frequently referred to as "activation" and the product is called an "activated poly(alkylene oxide)". Polymers containing both alpha and omega linking groups are referred to as bis-activated poly-alkylene oxides. Other substantially non-antigenic polymers are similarly "activated" or functionalized. Among the substantially non-antigenic polymers, bis-activated polyalkylene oxides (PAO's), such as bis-polyethylene glycols are preferred. Moreover, homobifunctional bis-activated polymers such as bis-succinimidyl carbonate activated PEG are especially preferred.

The activated polymers are thus suitable for reacting with interferon and forming IFN-polymer conjugates wherein attachment preferably occurs at either the amino terminal $\alpha$-amino group or $\epsilon$-amino groups of lysines found on the IFN. Free carboxylic acid groups, suitably activated carbonyl groups, oxidized carbohydrate moieties can also be used as attachment sites for hydrazine or carbazate activated polymers. Mercapto groups, if available on the IFN, can also be used as attachment sites for suitably activated polymers.

In one preferred aspect of the invention, carbamate (urethane) linkages are formed using the IFN $\epsilon$ amino groups and the activated polyalkylene oxides. Preferably, the carbamate linkage is formed as described in commonly owned U.S. Pat. No. 5,122,614, the disclosure of which is hereby incorporated by reference. This patent discloses the formation of mono- and bis-N-succinimidyl carbonate derivatives of polyalkylene oxides. Alternatives include para-nitrophenyl carbonate and carbonyl imidazole activated polymers. In accordance with the present invention, however, the activated polymer is used only in the molar ratios defined herein, i.e. from about 0.125 to about one mole per mole of interferon rather than the substantial molar excesses taught in the '614 patent.

In another aspect of the invention, polymers activated with amide-forming linkers such as cyclic imide thine-activated polyalkylene oxides, succinimidyl esters or the like are used to effect the linkage between the interferon and polymer terminal groups, see for example, U.S. Pat. No. 5,349,001 to Greenwald, et al., the disclosure of which is incorporated herein by reference. Still other aspects of the invention include using other activated polymers to form covalent linkages of the polymer with the interferon via $\epsilon$ amino or other groups. For example, isocyanate or isothiocyante forms of terminally activated polymers can be used to form urea or thiourea-based linkages with the lysine amino groups. PEG-dialdehyde can also be reacted with the interferon followed by reduction with $NaCNBH_3$ to form a secondary amine linkage.

Suitable polymers will vary substantially by weight, however polymers having molecular weights ranging from about 600 to about 60,000 are usually selected for the purposes of the present invention. Molecular weights of from about 1,000 to about 40,000 are preferred and 2000 to about 20,000 are particularly preferred.

The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained.

As an alternative to PAO-based polymers, effectively non-antigenic materials such as dextran, polyvinyl pyrrolidones, polyacrylamides, polyvinyl alcohols, carbohydrate-based polymers and the like can be used. Indeed, the activation of alpha and omega terminal groups of these polymeric substances can be effected in fashions similar to that used to convert polyalkylene oxides and thus will be apparent to those of ordinary skill. Those of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

3. REACTION CONDITIONS

Conjugation reactions, sometimes referred to as pegylation reactions, are generally carried out in solution with molar excess of polymer and without regard to where the polymer will attach to the protein. Such general techniques, however, have been proven to be inadequate for conjugating interferons to non-antigenic polymers and retain sufficient interferon activity. One way to maintain the interferon bioactivity is to substantially avoid including those interferon lysines associated with the active site in the polymer coupling process. The process of the present invention provides conjugates having high levels of retained activity by avoiding the use of several-fold molar excesses of activated polymer during the conjugation reactions.

The conditions under which the processes of the present invention are carried out also include reacting an interferon with a suitably activated bis-activated substantially non-antigenic polymer such as a bis-activated PEG in a suitable buffer solution in a ratio of bis-activated polymer to interferon of from about 0.125:1 to about 1:1. In separate embodiments, the upper limit for the amount of polymer included in the conjugation reactions exceeds "about one" to the extent that it is possible to react the activated polymer and interferon without forming a substantial amount of high molecular weight species, i.e. more than about 20% of the conjugates containing more than about one strand of polymer per molecule of interferon. For example, it is contemplated in this aspect of the invention that ratios of up to about two:one can be employed to form significant amounts of the desired conjugates which can thereafter be isolated from any high molecular weight species.

The conjugation reaction is carried out under relatively mild conditions to avoid inactivating the interferon. Mild conditions include maintaining the pH of the reaction solution in the range of 6–8 and the reaction temperatures within the range of from about 0°–30° C. and preferably about room temperature, i.e. 19°–22° C. A non-limiting list of suitable buffers includes phosphate, citrate, acetate, etc.

These reaction conditions are to be contrasted with those typically used for polymeric conjugation reactions wherein the activated polymer is present in several-fold molar excesses with respect to the target. In preferred aspects of the invention, the polymer is present in amounts of from about 0.25 to about 0.75 equivalents per equivalent of interferon. Most preferred aspects of the invention include reacting about 0.25 to about 0.5 equivalents of polymer per equivalent of interferon. Although the reaction conditions described herein can result in significant amounts of unmodified interferon, the unmodified interferon can be readily recycled into future batches for additional conjugation reactions.

In spite of the process of the present invention including bis-activated forms of polymer to form the polymer conjugates, the processes of the present invention generate surprisingly very little, i.e. less than about 5% and more preferably, less than about 3%, of high molecular weight species and species containing more than one polymer strand per interferon. While applicants are not bound by theory, it is believed that looping of the polymer in a protective fashion or steric hindrance inhibits generation of high molecular weight species and species containing more than one polymer strand per interferon.

The conjugation reactions of the present invention initially provide a reaction mixture or pool containing mono- and bis-interferon conjugates, unreacted interferon, unreacted polymer and usually less than about 5% high molecular weight species. The high molecular weight species include conjugates containing more than one polymer strand and/or polymerized PEG-IFN species. After the unreacted species and high molecular weight species have been removed, compositions containing primarily mono- and bis-interferon-polymer conjugates are recovered. Given the fact that the conjugates for the most part include a single polymer strand, the conjugates are substantially homogeneous. These compositions have at least about 60% of the biological activity associated with the native or unmodified interferon as measured using a standard viral protection assay, such as a CPE assay with EMC virus challenging A549 human lung carcinoma cells. See, for example, Larocca, A. T., Borden, E. C., and Colby, C. B. in *Human Cytokines, Handbook for Basic & Clinical Research*. B. B. Aggarwal & S. U. Gutterman (eds.), Blackwell Scientific Publications, Boston, 1991. The disclosure of the foregoing reference is incorporated by reference herein. In preferred aspects of the invention, however, the mixture has about 75% of the biological activity associated with unmodified interferon and most preferably, the mixture has about 90% of the biological activity associated with unmodified interferon.

The processes of the present invention preferably include rather limited ratios of polymer to interferon. Thus, the interferon conjugates have been found to be predominately limited to species, (mono- or bis-) containing only one strand of polymer. Furthermore, the attachment of the polymer to the interferon lysines is substantially less random than when higher molar excesses of polymer linker are used. For example, depending upon the molar ratios used, the conjugation reactions undertaken in accordance with the present invention yield pools containing a combination of mono- and bis-interferon polymer conjugates in ratios (based on protein content) ranging from about 1:1 to about 5:1 mono:bis, preferably about 3:1 mono:bis and most preferably about 2:1 mono:bis.

A representative conjugation reaction is set forth below:

about 0.125 to about 1 mole of bis-activated polymer is dissolved in Water For Injection (pH approximately 6.0) and then added to an interferon solution adjusted to about pH 6.5 with a suitable buffer such as a phosphate buffer. The reaction is allowed to incubate at room temperature (approximately 20°–25° C.) for a suitable time, such as about 2 hours, with continuous gentle mixing. Thereafter, the conjugation reaction is stopped with a several-fold molar excess of glycine. The resultant reaction solution or pool of conjugates contains (based on protein content) from about 1:1 to about 5:1 mono-:bis-interferon-polymer-conjugates. The unmodified interferon present in the reaction pool, after the conjugation reaction has been quenched, can be recycled into future reactions using ion exchange or size exclusion chromatography or similar separation techniques. Preferably, the compositions of the present invention contain less than about 5% unmodified interferon.

4. ISOLATION OF MONO- AND BIS-CONJUGATES

In a further embodiment of the invention, the mono- and bis-interferon-polymer species are isolated from the reaction mixture to remove high molecular weight species, and unmodified interferon. Separation is effected by placing the mixed species in a buffer solution containing from about 1–10 mg/ml of the interferon-polymer conjugates. Suitable solutions have a pH of from about 6.0 to about 9.0 and preferably from about 7.5 to about 8.5. The solutions preferably contain one or more buffer salts selected from KCl, NaCl, $K_2HPO_4$, $KH_2PO_4$, $Na_2HPO_4$, $NaH_2PO_4$, $NaHCO_3$, $NaBO_4$, and NaOH. Sodium phosphate buffers are preferred.

Depending upon the reaction buffer, the interferon polymer conjugate solution may first have to undergo buffer exchange/ultrafiltration to remove any unreacted polymer. For example, the PAO-Interferon conjugate solution can be ultra-filtered across a low molecular weight cut-off (10,000 to 30,000 Dalton) membrane to remove most unwanted materials such as unreacted polymer, surfactants, if present, or the like.

The fractionation of the conjugates into a pool containing the desired mono- and bis-species is preferably carried out using an anion exchange chromatography medium. Such media are capable of selectively binding PAO-interferon conjugates via differences in charge which vary in a somewhat predictable fashion. For example, the surface charges of αIFN is determined by the number of available charged amino acids on the surface of the protein. Of these charged amino acids, lysine residues serve as the point of potential attachment of polyalkylene oxide conjugates. Therefore, mono and bis-interferon conjugates will have a different charge from the other species to allow selective isolation.

The use of strongly polar anion exchange resins such as quaternary amine anion exchange resins are especially preferred for the method of the present invention. Included among the commercially available quaternary anion exchange resins suitable for use with the present invention are Q-HD, QA TRISACRYL® and QMA-SPHEROSIL®, quaternary amine resins coated onto a polymer matrix, manufactured by IBF of Garenne, France, for Sepracor of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by ToSoHaas of Montgomeryville, Pa. QMA Accell, manufactured by Millipore of Millford, Mass. and PEI resins manufactured by J. T. Baker of Phillipsburg, N.J., may also be used. Other suitable anion exchange resins e.g. DEAE resins can also be used.

For example, the anion exchange resin is preferably packed in a column and equilibrated by conventional means. A buffer having the same pH and osmolality as the polymer conjugated interferon solution is used. The elution buffer preferably contains one or more salts selected from KCl, NaCl, $K_2HPO_4$, $KH_2PO_4$, $Na_2HPO_4$, $NaH_2PO_4$, $NaHCO_3$, $NaBO_4$ and $(NH_4)_2CO_3$. The conjugate-containing solution is then adsorbed onto the column with the high molecular weight species and unreacted polymer not being retained. At the completion of the loading, a gradient flow of an elution buffer with increasing salt concentrations is applied to the column to elute the desired fraction of polyalkylene oxide-conjugated interferon. The eluted pooled fractions are preferably limited to uniform mono- and bis-interferon polymer conjugates after the anion exchange separation step. Any unconjugated interferon species can then be back washed from the column by conventional techniques. If desired, mono- and bis-interferon species can also be separated from each other via additional ion exchange chromatography or size exclusion chromatography.

Techniques utilizing multiple isocratic steps of increasing concentration can also be used. Multiple isocratic elution steps of increasing concentration will result in the sequential elution of mono- and then bis-interferon-polymer conjugates.

The temperature range for elution is between about 4° C. and about 25° C. Preferably, elution is carried out at a temperature of from about 6° C. to about 22° C. For example, the elution of the PAO-αIFN fraction is detected by UV absorbance at 280 nm. Fraction collection may be achieved through simple time elution profiles.

5. SURFACTANTS

In another aspect of the invention, a surfactant is used in the processes of the present invention. Suitable surfactants include ionic-type agents such as sodium dodecyl sulfate, (SDS). Other ionic surfactants such as lithium dodecyl sulfate, quaternary ammonium compounds, taurocholic acid, caprylic acid, decane sulfonic acid, etc can also be used. Non-ionic surfactants can also be used. For example, materials such as polyoxyethylene sorbitans (Tweens), polyoxyethylene ethers (Tritons) can be used. See also Neugebauer, *A Guide to the Properties and Uses of Detergents in Biology and Biochemistry* (1992) Calbiochem Corp. The only limitations on the surfactants used in the processes of the invention are that they are used under conditions and at concentrations that do not cause substantial irreversible denaturation of the interferon and do not completely inhibit polymer conjugation. The surfactants are present in the reaction mixtures in amounts from about 0.01–0.5%; preferably from 0.05–0.5%; and most preferably from about 0.075–0.25%. Mixtures of the surfactants are also contemplated.

While applicants are not bound by theory, it is thought that the surfactants provide a temporary, reversible protecting system during the polymer conjugation process. For example, αIFN contains three lysines in the active site region. This relatively positive-charged area of the polypeptide has been found to undergo substantial polymer conjugation during solution-based processes without some kind of protection especially when molar excesses of polymer are used. This results in substantial or complete loss of bioactivity. The surfactants have been found to be surprisingly effective in selectively discouraging polymer conjugation in this area while allowing lysine-based or amino terminal-based conjugation to proceed on other areas of the polypeptide.

6. METHODS OF TREATMENT

Another aspect of the present invention provides methods of treatment for various medical conditions in mammals. The methods include administering an effective amount of interferon-polymer conjugates which have been prepared as described herein to a mammal in need of such treatment. The conjugates are useful for, among other things, treating interferon-susceptible conditions or conditions which would respond positively or favorably as these terms are known in the medical arts to interferon-based therapy. Thus, without limitation, the interferon conjugates can be used to treat conditions which would benefit from the inhibiting replication of interferon-sensitive viruses. In addition, the conjugates can be used to modify various immune responses including inhibition of antibody response to antigenic challenge, inhibition of hypersensitivity reactions, regulation of NK cell activity enhancement of cytotoxic T cell activity, modulation of prostaglandin production and enhancement of phagocytosis by macrophages.

Additional conditions in which the interferon-polymer conjugates can be used include hairy cell leukemia, venereal or genital warts (condylomata acuminata), AIDS-Related Kaposi's sarcoma, hepatitis and hepatitis-like viral conditions including hepatitis-B and chronic hepatitis non-A, non-B/C, and various solid tumors.

The amount of the interferon-polymer conjugate administered to treat the conditions described above is based on the interferon activity of the polymeric conjugate. It is an amount that is sufficient to significantly effect a positive clinical response. The maximal dose for mammals including humans is the highest dose that does not cause clinically-important side effects. For purposes of the present invention, such clinically important side effects are those which would require cessation of therapy due to severe flu-like symptoms, central nervous system depression, severe gastrointestinal disorders, alopecia, severe pruritus or rash. Substantial white and/or red blood cell and/or liver enzyme abnormalities or anemia-like conditions may also be dose limiting.

Naturally, the dosages of the interferon-based compositions will vary somewhat depending upon the interferon moiety and polymer selected. In general, however, the conjugate is administered in amounts ranging from about 100,000 to about several million IU/m$^2$ of interferon per day, based on the mammal's condition. The range set forth above is illustrative and those skilled in the art will determine the optimal dosing of the conjugate selected based on clinical experience and the treatment indication.

The IFN-polymer conjugates and compositions containing the mono- and bis-interferon polymer conjugates of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions will be chiefly by the parenteral route although oral or inhalation routes may also be used depending upon the needs of the artisan.

EXAMPLES

The following examples serve to provide further appreciation of the invention but are not meant in any way to restrict the effective scope of the invention.

Example 1

In this example, bis-succinimidyl carbonate-activated polyethylene glycol, molecular weight 8,000, was used to modify alpha interferon. The bis-succinimidyl carbonate activated PEG was prepared in accordance with the method of the aforementioned U.S. Pat. No. 5,122,614. The interferon was recombinant αIFN-2b, (rαIFN), a product of the Schering Plough Corporation, Madison, N.J.

Interferon alpha (0.28 μmoles 5 mg) was adjusted to pH 6.5 with 100 mM phosphate buffer. The activated PEG was dissolved in Water For Injection (pH approximately 6.0) and then added to the alpha interferon in a ratio of about one-half mole of bis-activated polymer per mole of interferon. The reaction was incubated at room temperature (21° C.) for about 2 hours with continuous gentle mixing. After 2 hours, the reaction was stopped with a ten-fold molar excess of glycine. The reaction products were analyzed via SEC-HPLC (BioRad, Bio-Sil SEC-125 column) at a flow rate of 1.0 ml/minute using a 0.1 molar phosphate buffer, pH 7.0 with detection at 280 nm. The results of HPLC analysis were as follows:

TABLE 1

| RETENTION TIME | % PEAK AREA | COMMENTS |
| --- | --- | --- |
| 7.32 | 3 | High molecular weight species |
| 7.51 | 3 | High molecular weight species |
| 7.78 | 14 | BIS-IFN-PEG |
| 8.29 | 29 | Mono-IFN-PEG |
| 10.1 (native) | 50 | Unmodified IFN |

Referring to Table 1, it can be seen that the reaction mixture contained (on the basis of interferon protein) about 50% modified interferon and about 50% unmodified interferon. The modified interferon is further defined as containing about 6% (3+3) higher modified forms of IFN-polymer conjugates, about 14% bis-interferon-polymer conjugates and approximately 29% mono-interferon polymer conjugates. Thus, the ratio of mono to bis conjugates in the reaction mixture solution was about 2:1. A pool containing the unreacted interferon, mono- and bis-interferon conjugates was recovered using SEC-HPLC.

Example 2

The process of Example 1 was repeated except that the molar ratio of bis-activated PEG to interferon was about 1:1. The results of the HPLC analysis are set forth below in Table 2.

TABLE 2

| RETENTION TIME | % PEAK AREA | COMMENTS |
| --- | --- | --- |
| 7.43 | 3 | High molecular weight species |
| 7.85 | 9 | BIS-IFN-PEG |
| 8.3 | 29 | Mono-IFN-PEG |
| 10.05 | 59 | Unmodified IFN |

In this particular example, it can be seen that peak areas corresponding to all conjugated species are somewhat less than those observed using the reaction conditions of Example 1. In particular, the level of high molecular weight species (interferon conjugated with multiple polymer strands or polymerized species) is about 3%. Thus, in spite of doubling the number of equivalents of polymer present in the conjugation reaction, the amount of high molecular weight species actually decreased. About 9% of the interferon was transformed into bis-IFN-PEG conjugates and approximately 29% of the interferon was converted into Mono-IFN-PEG. About 59% of the interferon was unmodified. Under these conditions, the reaction pool was found to contain a ratio of about 3:1 mono to bis conjugates. As was the case in Example 1, the high molecular weight species were separated from the pool containing the remaining IFN species.

Example 3

In this example, the IFN and PEG-IFN conjugate pools of Examples 1 and 2 were purified via SEC-HPLC to remove unmodified IFN to levels of less than 2%. The purified conjugate pools were then concentrated and assayed for biological activity. The results were then compared to unmodified alpha interferon. Activity was determined using a CPE assay with EMC virus challenging A549 human lung carcinoma cells.

TABLE 3

| IFN SAMPLE | VIRAL PROTECTION ASSAY IC$_{50}$ (pg/ml) | ACTIVITY (%) |
| --- | --- | --- |
| unmodified IFN | 0.31 | 100 |
| Example 1 pool | 0.33 | 94 |
| Example 2 pool | 0.36 | 86 |

As can be seen from the results, the compositions obtained from the process of Example 1 had a CPE activity which nearly equaled that of unmodified IFN. CPE activity decreased as the ratio of mono- to bis-interferon conjugates in the reaction solutions increased. For example, CPE activity was greatest with the Example 1 pool (mono:bis=2:1) and lower when the ratio of mono to bis was increased. It was postulated that when the ingredients were reacted in low polymer-interferon molar ratios, the bis-activated polymer attached to the interferon in a less random manner which led to greater retained activity. Another possibility is that bis-IFN-PEG may be more potent than mono-IFN-PEG at cross-linking and "capping" IFN receptors on A549 cells, resulting in enhanced biological activity.

Example 4

In this example, recombinant αIFN-2b, (rαIFN) was conjugated with activated ω-methoxy-polyethylene glycol-α-N-succinimidyl carbonate (SC-mPEG) as described in U.S. Pat. No. 5,122,614. The polymer had a molecular weight of about 5,000.

Approximately 36 mg of the rαIFN was dialyzed into 0.1 molar sodium phosphate pH 7.5 using a Centricon-10 (a product of the Amicon Corporation of Beverly, Mass.). The final concentration of rαIFN was about 3 mg/ml. Thereafter, 42 mg of SC-mPEG$_{5000}$ was added to the protein-solution and stirred at room temperature for two hours and then quenched with glycine. Next, the reaction mixture was dialyzed into 10 mM sodium phosphate pH 8 to fractionate the PEGylated IFN using a Centricon-30. The resulting conjugates were determined to have about 4 strands of polymer per interferon. A viral protection assay was performed in the same manner as that conducted for the bis-IFN conjugates and the amount of retained activity, calculated via CPE, was found to be only about 30% of the unmodified interferon assayed at the same time.

From the foregoing, it can be determined that the bis-activated polymers have significant advantages over mono-activated polymers for modifying interferons. Further, it can also be seen that the molar ratios of reaction ingredients used in the processes of the present invention also have unexpected advantages over the molar excesses used in the past.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A process for preparing interferon-polymer conjugates, comprising: reacting an interferon with a bis-activated substantially non-antigenic polymer in a molar ratio of substantially non-antigenic polymer to interferon of from about 0.125:1 to about 1:1 under conditions sufficient to effect covalent conjugation of said interferon and said polymer and form a reaction mixture containing mono-interferon-polymer conjugates and bis-interferon polymer conjugates wherein the bis-interferon polymer conjugates contain a single strand of substantially non-antigenic polymer with two molecules of interferon covalently attached to said polymer, one to the alpha terminus and one to the omega terminus of the polymer.

2. The process of claim 1, wherein said molar ratio of said bis-activated substantially non-antigenic polymer to said interferon is from about 0.25:1 to about 0.75:1.

3. The process of claim 2, wherein said molar ratio of said bis-activated substantially non-antigenic polymer to said interferon is from about 0.25:1 to about 0.5:1.

4. The process of claim 1, wherein said substantially non-antigenic polymer comprises a polyalkylene oxide.

5. The process of claim 4, wherein said polyalkylene oxide is a polyethylene glycol.

6. The process of claim 5, wherein said polyethylene glycol comprises a terminal carbamate linkage-forming moiety prior to said reacting.

7. The process of claim 6, wherein said carbamate linkage-forming moiety is selected from the group consisting of succinimidyl carbonate, para-nitrophenyl carbonate, and carbonyl imidazole.

8. The process of claim 5, wherein said polyethylene glycol comprises a terminal amide linkage-forming moiety prior to said reacting.

9. The process of claim 8, wherein said terminal amide linkage-forming moiety is selected from the group consisting of cyclic imide thiones and succinimidyl esters.

10. The process of claim 1, wherein said reaction mixture contains interferon in a ratio of about 2:1 mono- to bis-interferon conjugates.

11. The process of claim 10, wherein said substantially non-antigenic polymer has a molecular weight of from about 2,000 to about 20,000.

12. The process of claim 1, wherein said substantially non-antigenic polymer has a molecular weight of from about 600 to about 60,000.

13. The process of claim 1, wherein said reaction mixture contains interferon in a ratio of from about 1:1 to about 5:1 mono- to bis-interferon conjugates.

14. The process of claim 13, wherein said reaction mixture contains interferon in a ratio of about 3:1 mono- to bis-interferon conjugates.

15. The process of claim 14, wherein said substantially non-antigenic polymer has a molecular weight of from about 1,000 to about 40,000.

16. The process of claim 1, further comprising separating said mono- interferon-polymer conjugates and said bis-interferon-polymer conjugates from said reaction mixture.

17. The process of claim 16, further comprising isolating said mono- interferon-polymer conjugate from said bis-interferon-polymer conjugates.

18. The process of claim 1, wherein said interferon is selected from the group consisting of alpha interferons, beta interferons and gamma interferons.

19. The process of claim 1, wherein said interferon is an alpha interferon.

20. The process of claim 19, wherein said alpha-interferon is interferon alpha 2b.

21. The process of claim 1, wherein said interferon is ruminant interferon.

22. The process of claim 1, wherein said interferon is ruminant interferon.

23. The process of claim 21, wherein said ruminant interferon is bovine interferon.

24. The process of claim 21, wherein said human interferon is produced via recombinant techniques.

25. The process of claim 1, wherein said substantially non-antigenic polymer is selected form the group consisting of dextran, polyvinyl pyrrolidones, polyacrylamides, polyvinyl alcohols and carbohydrate-based polymers.

26. The process of claim 1, wherein said conditions sufficient to effect covalent conjugation of said interferon and said polymer include a surfactant.

27. The process of claim 26, wherein said surfactant comprises sodium dodecyl sulfate (SDS).

28. Interferon-polymer conjugate mixture prepared by the process of claim 1.

29. An interferon-substantially non-antigenic polymer conjugate-containing composition, comprising a ratio of from about 1:1 to about 5:1 mono-interferon-polymer conjugates and bis-interferon-polymer conjugates wherein the bis-interferon polymer conjugates contain a single strand of substantially non-antigenic polymer with two molecules of interferon covalently attached to said polymer, one to the alpha terminus and one to the omega terminus of the polymer.

30. The composition of claim 29, wherein said ratio is about 3:1 mono-interferon polymer conjugates to bis-interferon-polymer conjugates.

31. The composition of claim 29, wherein said ratio is about 2:1 mono-interferon polymer conjugates to bis-interferon-polymer conjugates.

32. The composition of claim 29, wherein the substantially non-antigenic polymer is a polyethylene glycol.

33. The composition of claim 29, wherein the conjugates include a carbamate linkage between the interferon and substantially non-antigenic polymer.

34. The composition of claim 29, wherein said conjugates include an amide linkage between the interferon and substantially non-antigenic polymer.

35. The composition of claim 29, wherein the substantially non-antigenic polymer has a molecular weight of from about 600 to about 60,000.

36. The composition of claim 35, wherein the substantially non-antigenic polymer has a molecular weight of from about 1,000 to about 40,000.

37. The composition of claim 36, wherein the substantially non-antigenic polymer has a molecular weight of from about 2,000 to about 20,000.

38. The composition of claim 29, wherein the interferon is selected from the group consisting of alpha interferons, beta interferons and gamma interferons.

39. The composition of claim 29, wherein said interferon is alpha interferon.

40. The composition of claim 29, wherein said interferon-substantially non-antigenic polymer conjugate-containing composition has about 60% of the biological interferon activity associated with unmodified interferon.

41. The composition of claim 40, wherein said interferon-substantially non-antigenic polymer conjugate-containing composition has about 75% of the biological interferon activity associated with unmodified interferon.

42. The composition of claim 41, wherein said interferon-substantially non-antigenic polymer conjugate-containing composition has about 90% of the biological interferon activity associated with unmodified interferon.

43. The composition of claim 29, wherein the interferon is interferon alpha 2b.

44. A method of treating an interferon-susceptible condition in mammals, comprising administering an effective amount of the composition of claim 29.

45. An interferon-substantially non-antigenic polymer conjugate-containing composition, consisting of mono-interferon-polymer conjugates and bis-interferon polymer conjugates and a pharmaceutically acceptable carrier.

46. An interferon containing composition comprising conjugates containing a single strand of substantially non-antigenic polymer having two molecules of interferon covalently attached to said polymer, one on the alpha terminus and one on the omega terminus of said polymer and a pharmaceutically acceptable carrier.

* * * * *

UNITED STATES PATENT AND TRADEMARK OFFICE
CERTIFICATE OF CORRECTION

PATENT NO. : 5,738,846

DATED : April 14, 1998

INVENTOR(S) : GREENWALD, Richard B., et al

It is certified that error appears in the above-identified patent and that said Letters Patent is hereby corrected as shown below:

Claim 21, line 2: change "ruminant" to --human--;

Claim 23, line 1: change "claim 21" to --claim 22--.

Signed and Sealed this

Eighth Day of September, 1998

Attest:

BRUCE LEHMAN

Attesting Officer

Commissioner of Patents and Trademarks